United States Patent [19]

Korman

[11] Patent Number: 5,686,303

[45] Date of Patent: Nov. 11, 1997

[54] METHOD OF GROWING VERTEBRATE SKIN IN VITRO

[76] Inventor: Joshua Korman, 47 Turn Suden Way, Woodside, Calif. 94062

[21] Appl. No.: 367,062

[22] Filed: Dec. 30, 1994

[51] Int. Cl.⁶ ............................... C12N 5/00; C12N 5/02; A61F 2/10

[52] U.S. Cl. .................... 435/325; 435/367; 435/371; 435/398; 435/402; 673/15

[58] Field of Search ................... 435/240.2, 240.23, 435/240.241, 240.242, 325, 367, 371, 318, 402; 623/15

[56] References Cited

U.S. PATENT DOCUMENTS

| | | | |
|---|---|---|---|
| 3,640,279 | 2/1972 | Brown et al. | 435/240.2 |
| 4,673,649 | 6/1987 | Boyce et al. | 435/240.2 |

OTHER PUBLICATIONS

Argenta, L.C. et al., (1983) "The Use of Tissue Expansion in Head and Neck Reconstruction," *Ann. Plast. Surg.* 11:31–37.

Argenta, L.C. (1984) "Controlled Tissue Expansion in Reconstructive Surgery," *Brit. J. Plas. Surg.* 37:520–529.

Hiernickel, H. (1985) "An Improved Method For In Vitro Perfusion of Human Skin," *British Journal of Dermatology* 112:299–305.

Carney, S.A. (1986) "Generation of Autograft; The State of the Art," *Burns* 12:231–235.

Eldad, A. et al., (1987) "Cultured Empithelium as a Skin Substitute," *Burns* 13(3):173–180.

Gallico III, G.G. (1990) "Biologic Skin Substitutes," *Clinics In Plastic Surgery* 17(3):519–526.

Nanchahal, J. and C.M. Ward, (1992) "New Grafts For Old? A Review of Alternatives to Autologous Skin," *British Journal of Plastic Surgery* 45:354–363.

Dennis, L.W. (1992) "Tissue Cultured Skin Grafts," *Journal of Burn Care & Rehabilitation* 13(1):93–94.

Arons, J.A. et al., (1992) "The Surgical Applications and Implications of Cultured Human Epidermis: A Comprehensive Review," *Surgery* 111(1):4–11.

Greenwald, D.P. et al., (1992) "Full–Thickness Skin Wound Explants in Tissue Culture: A Mechanical Evaluation of Healing," *Plastic and Reconstructive Surgery* 90(2):289–294.

Wong, L. and A.M. Munsten, (1993) "New Techniques in Burn Wound Management," *Surgical Clinics of North America* 73(2):363–371.

Kirsner, R.S. et al., (1993) "The Biology of Skin Grafts," *Arch Dermatol* 129:481–483.

Teepe, R.G.C. et al., (1993) "Randomized Trial Comparing Cryopreserved Cultured Epidermal Allografts With Tulle–Gras in the Treatment of Split–Thickness Skin Graft Donor Sites," *The Journal of Trauma* 35(6):850–854.

Tanner, James C. et al. (1964) "*Plastic and Reconstructive Surgery,*" 34:287–292.

Tanner, James C. et al. (1966) "*American Journal of Surgery,*" 111:543–547.

Tanner, James C. et al. (1969) "*Plastic and Reconstructive Surgery,*" 44:504–506.

*Primary Examiner*—Blaine Lankford
*Attorney, Agent, or Firm*—Cooley Godward LLP

[57] ABSTRACT

A method of growing complete vertebrate skin in vitro, which comprises obtaining a segment of vertebrate skin, positioning the skin segment in an artificial cell-growth medium containing sufficient nutrients to maintain growth of cells of the skin, and subjecting the skin segment to stretching forces while the skin segment is in the medium. Skin produced by the method and an apparatus for carrying out the method are also part of the present invention.

10 Claims, 1 Drawing Sheet

METHOD OF GROWING VERTEBRATE SKIN IN VITRO

TECHNICAL FIELD

This invention is in the field of cell and tissue culture and is particularly directed to the production of vertebrate skin having both a dermal layer and an epidermal layer.

BACKGROUND

Vertebrate skin is a complex organ comprising two principal layers, an outer epidermal layer and a dermal layer lying under the epidermal layer. In order for skin to retain its normal appearance and to function fully in a normal manner, both layers of the skin need to be present.

Skin grafting is an essential component of reconstructive surgery after burns, trauma, tumor excision, and correction of congenital anomalies. There are approximately 1 million burns per year in the U.S. alone, which result in about 100,000 admissions to burn units, about ½ of which require skin grafting. Skin grafting in reconstructive surgery is often required to alleviate deformity. The best possible skin available for grafting would be skin from the same patient taken from a donor site elsewhere on the body (referred to as an autograft). Suitable skin graft donor sites, however, are limited not only by body surface area, but can also be affected by previous graft harvest or trauma. There are times, therefore, when donor skin is limited and the amount of skin required for grafting is quite large, so that sufficient autografts are not available. Because of the importance of the skin in preventing infection, either the donor skin must be used to cover a larger area than it originally covered or some suitable replacement material must be used.

Currently, several techniques are used to enhance the amount of donor area skin. Meshing of donor skin (slitting the skin to form an expandable mesh pattern) is used to increase the total area of graft. However, meshing is only minimally able to increase graft size while it significantly detracts from the appearance of grafts, making them unacceptable for reconstruction on the face, and far from ideal on the hands, arms, and neck. In patients suffering from large burns with limited donor skin sites, cadaver allografts are commonly used for temporary skin coverage, but ultimately such allografts are rejected, and a permanent autograft is required. In addition, allografts also pose a risk of infection of the recipient by viruses or other disease-causing organisms present in the donor, such as infection by human immunodeficiency virus or hepatitis virus.

To aid in the grafting of patients with limited donor areas, cultured epithelial cells derived from the patient being treated have been utilized in many grafting applications. In general, the cells are used in the form of a monolayer of epithelial cells grown on a culture medium. Preparation of such cultures requires many weeks or months, and the product is quite difficult to handle because of its fragility, even when multiple epidermal cell layers are used to form a multi-layer skin substitute.

Harvesting of multiple skin grafts from the same donor site is often used, but such harvesting requires weeks to months between procedures for new skin to grow on the donor site. It is also a very traumatic technique, since multiple painful operations must be undertaken.

Tissue expansion techniques, which are in vivo techniques, have been used in plastic surgery for over a decade and can be helpful in increasing the area of donor tissue. By placing an expander subcutaneously and frequently injecting it with saline, skin can be expanded and its surface area increased. This allows reconstruction with local skin after expansion of an adjacent tissue bed. Expanders are not ideal, however, because they require multiple procedures. When local tissue is of poor quality, as might be the case in a patient who has undergone multiple reconstructions or irradiation or has been burned, expanders are not a viable option. For examples of the general application of tissue expansion, see, for example, Argenta, "Controlled tissue expansion in reconstructive tissue," Brit. J. Plas. Surg., 37:520–529 (1984), and Argenta et at., "The Use of Tissue Expansion in Head and Neck Reconstruction," Ann. Plast. Surg., 11:31–37 (1983).

Additional background information in the general field of skin grafting is available in the scientific literature. A number of exemplary publications are cited below:

Kirsner et al, "The Biology of Skin Grafts," Arch. Dermatol., 129:481–483 (1993).

Gallico, "Biologic Skin Substitutes," Clinics in Plastic Surgery, 17:519–526 (1990).

Nanchahal and Ward, "New grafts for old? A review of alternatives to autologous skin," Brit. J. Plas. Surg., 45:354–363 (1992).

Carney, "Generation of autograft; the state of the art," Burns. 12:231–235 (1986).

Greenwald et at., "Full-Thickness Skin Wound Explants in Tissue Cultures: A Mechanical Evaluation of Healing," Plastic and Reconstructive Surgery, 90:289–294 (1992).

Arons et at., "The surgical applications and implications of cultured human epidermis: A comprehensive review," Surgery, 111:4–11 (1992).

In view of the shortcomings of the prior art recited above, a technique that provides a large surface area of normal skin from a small donor skin segment is therefore needed. Desirably, the skin should be an autograft and should be available in as short a time period as possible. Such a technique would be of great benefit to a reconstructive surgery patient because it would limit the number of surgical procedures required on a patient. It will also potentially increase survival by closing wounds more promptly in a patient who requires a large amount of skin grafting.

BRIEF DESCRIPTION OF THE DRAWINGS

Certain aspects of the invention will be better understood by reference to the drawing that form part of the specification, wherein.

SUMMARY OF THE INVENTION

Figure 1:
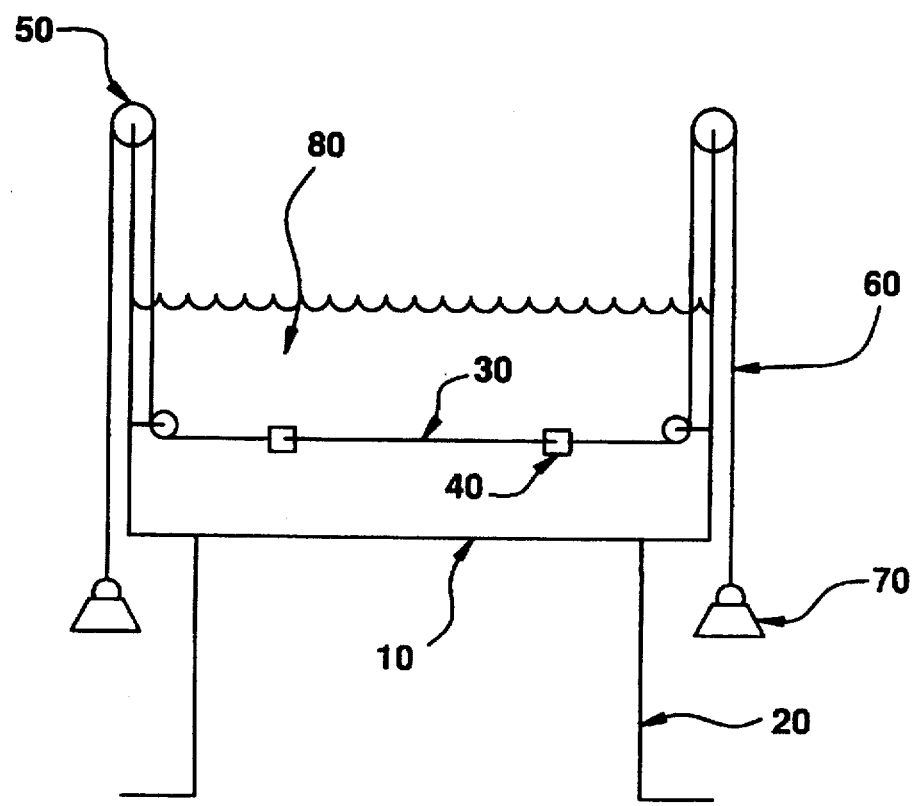
FIG. 1 is a vertical cross-sectional view of a first embodiment of an apparatus of the invention.

Accordingly, it is an object of the invention to provide a method of producing a normal skin autograft.

It is a further object of the invention to provide a normal skin autograft having a larger surface area than the area of the donor graft site.

It is yet another object of the invention to provide a normal skin autograft in as sort a time period as possible.

It is a still further object of the invention to provide hair- or fur-bearing skin that can be produced in large quantities in vitro.

These and other objects of the invention have been accomplished by providing a method of growing vertebrate skin in vitro, which comprises obtaining a segment of vertebrate skin containing an epidermal layer and at least part of the normal dermal layer, positioning said skin segment in an artificial cell-growth medium containing sufficient nutrients to maintain growth of cells of said skin, and subjecting said skin segment to stretching forces while said skin segment is in said medium. Skin produced by this technique is also an object of the invention.

In various embodiments of the invention, the stretching forces are dynamic or static, orthogonal or radial, or constant or varying. The skin is preferably human for use in human recipients, but veterinary use of the new skin is also encompassed by the invention. Other embodiments of the invention are set forth below in detail.

DESCRIPTION OF SPECIFIC EMBODIMENTS

The present invention combines a number of previously known techniques in a novel manner to achieve results not previously obtained, namely normal autograft skin segments (containing both a dermal layer and an epidermal layer) that are larger than the autograft donor site and that are prepared in vitro. The method of the invention makes available durable autologous skin greatly increased in size available for transfer to either nearby or distant locations. By using stretching forces on skin in vitro during tissue culture, a goal of maximizing the potential availability of skin while decreasing patient morbidity associated with skin grafting can be achieved. In addition, problems which prior to now exist using allografts and cultured epithelial cells would not be encountered. Potentially this technique could save costs by minimizing the number of surgical procedures a patient would require while also decreasing the risk associated with multiple anesthetics and surgical procedures sometimes needed in cases of complex reconstruction.

There are a number of technologies ancillary to the present invention that are well developed and that thus will not be described here in great detail, such as methods for excision of the original skin segment, production of culture media for the growth and maintenance of intact skin, and grafting techniques for the attachment of the graft to the host. Such methods and materials are exemplified here, and references are given to scientific publications, where appropriate, so that the invention can readily be practiced. It will be recognized, however, by one of ordinary skill in the art, that many variations of these ancillary methods and materials exist and that the invention is not limited to the specific examples provided here.

In general, the method of the invention provides a method of growing complete vertebrate skin in vitro, which comprises obtaining a segment of vertebrate skin, positioning the skin segment in an artificial cell-growth medium containing sufficient nutrients to maintain growth of cells of the skin segment, and subjecting the skin segment to stretching forces while the skin segment is in the medium. Here "in the medium" means that at least the dermal side of the skin is in contact with the medium, since the epidermal layer of skin is normally exposed to air. However, the skin segment can be completely sumberged in the nutrient medium, if desired. When skin is present in a growth medium while being subjected to stretching forces, cell division and growth occur so as to produce normal, full-thickness skin having both a dermal layer and an epidermal layer. The skin produced in this manner is particularly suitable for grafting in place of complete skin loss (i.e., loss of both the dermal layer and the epidermal layer) and for other uses described herein.

In the following description of various embodiments of the invention, the invention is described in most cases as being practiced with a human skin autograft. However, the invention is not so limited and can be used for both allografts (within the same species, but with the donor and recipient being different individuals) and xenografts (donor and recipient from different species). Additionally, the invention is not limited to preparation of human skin, since it can be advantageously practiced to produce large amounts of normal skin of various vertebrates, either for veterinary use as autografts or allografts, or for use in the production of xenografts (which would normally require suppression of the immune system of the recipient when the product skin is used as a graft), since even the temporary protection against infection and sepsis provided by a xenograft may save the life of the recipient organism. For veterinary or xenograft use, the donor skin can be obtained from any vertebrate, preferably one related as closely as possible to the recipient. Non-exclusive examples include skin from humans, other primates, cattle and other domesticated bovines, pigs, hogs, cats, dogs, sheep, goats, birds, and reptiles. The method can also be used in the fur industry to produce artificial furs that do not require the sacrifice of animals, such as animals that are difficult to raise domestically or that are endangered, including sea otters, seals, tigers, and the like. Production of hair-bearing human skin for use in treating baldness is also a part of the invention. For the production of stretched skin with hair or fur, full-thickness skin is used, as split-thickness skin lacks hair follicles.

A segment of vertebrate skin (graft donor segment) is obtained by any of the techniques normally available for this purpose, usually surgical excision (for full-thickness skin) or use of a dermatome (for split-thickness skin). If a dermatome (i.e., any plane-like device for removing skin from a subject) is used, the thickness of the layer should be selected to ensure that at least some of the dermal layer is present. This thickness will vary from species to species and even from location to location on the body of an individual. A typical setting for a dermatome used to prepare split-thickness human skin is about 12/1000th of an inch (about 0.3 mm). The skin segment is obtained so that both dermal and epidermal layers are present in the detached segment. The dermal layer can be either complete (full-thickness skin) or incomplete (split-thickness skin), but some of the dermal layer should be present.

Full-thickness skin segments are generally obtained by surgical excision, while split-layer skin segments are obtained by a dermatome. Both of these techniques, as well as other general techniques in the field of skin grafting, as described in Chapter 1 (pp. 1–90) of Grabb and Smith, *Plastic Surgery*, Little Brown & Company, Boston, Mass., USA, 4th Ed. (1991), James W. Smith and Sherrel J. Aston, eds. The detached skin is normally transferred directly to a culture medium, and in most cases in not allowed to dry out before being positioned in the medium. The shape of the detached skin segment is not material to the practice of the invention, but certain shapes will be better suited to individual specific apparatus variations described here.

The size of the donor skin segment is generally selected for the convenience of use with the apparatus in which it will be stretched and may also vary depending on the availability of donor skin tissue of the same type as that being replaced. Typical human skin segments are from 1×1 cm to 10×30 cm but can vary significantly depending on the availability of donor skin. There is generally no impact of graft size on the method of the invention, so that surgical and other procedures generally are more important in determining tissue size. For ease of handling in surgical skin grafting, segments ranging in size from 5×5 cm to 15×15 cm are preferred.

Preparation and use of artificial cell-growth media containing sufficient nutrients to maintain growth of cells of a skin segment are well established techniques and need not be described here in detail. Such media are also referred to as nutrient media or tissue-culture media. Whether any given medium will be satisfactory (if not already known) can easily be determined experimentally using the procedures for skin growth set out in the examples below. Many such media are commercially available, such as Dulbecco's modified Eagle's medium (DMEM) with 10% added fetal calf serum. Other suitable media include basal medium (Eagle) with Hanks's BSS (85%) supplemented with calf serum (15%) and Ham's F12 medium (90%) supplemented with fetal bovine serum (10%). When serum is used to supplement an artificial medium, fetal serum is preferred, especially fetal serum from the same species as the recipient of the graft. When this is not possible or ethically desirable, the recipient's own serum can be used. For a number of media that can be used to grow skin tissue, see, for example, the media formulations section of any volume of the American Type Culture Collection publication entitled Catalogue of Cell Lines & Hybridomas (e.g., 5th edition, 1985, pages 265-273). This ATCC publication also contains information (in connection with specific skin-derived cell lines) on which media are best for use with tissue or cell cultures derived from skin.

The apparatus in which tissue culture and stretching takes place can vary widely, being either simple or complex. An example of a simple apparatus is a Petri (or similar) dish containing a tissue-culture medium and having a set of clamps, wires, pulleys, and weights arranged so that the clamps can be attached to a detached skin segment in the medium and subjected to forces applied to clamps by weights attached to the clamps by the wires and suspended by the pulleys to reduce friction. A more complex apparatus could contain electric motors for supplying force to the clamps or for circulating the culture medium in the apparatus, sensors to measure forces and stretching distances, reservoirs for fresh and waste medium, controlled atmospheres, and the like. Minimally, an apparatus of the invention will comprise a container for holding a tissue culture medium, at least two connectors for holding a detached skin segment in the culture medium at at least two locations on the skin segment, the connectors being attached to the container, and means for supplying opposing forces via the attachment means to the skin segment. The container may be an integral part of the apparatus or may be a separate container that is retained by the apparatus at a specific location. In the later case the connectors are "attached" indirectly to the container by being affixed to the frame of the apparatus that will hold the container.

An alternative apparatus can comprise a tubular fluid reservoir having an open end, a clamp located at the open end of the reservoir, where the clamp is adapted to seal the skin segment over the open end to provide a fluid-tight seal, and means for supplying hydrostatic pressure to a fluid located in the reservoir. It should be recognized here that "tubular" does not require a circular cross section, as the word is used here. Examples of means for supplying hydrostatic pressure comprises (1) a nutrient reservoir fluidly connected to the tubular fluid reservoir and being located at a higher gravitational potential than the skin segment when the apparatus is located in its normal operating position or (2) a pump fluidly connected to the tubular reservoir. A pump is any mechanical device that moves fluid from one location to another and includes a hydraulic piston. An example of a suitable clamp would be an annular member adapted to fit tightly against a flange on the open end of the tubular reservoir, with holes or grooves in the flange or annular member (or both) adapted to contain screws, bolts, wing nuts, or the like for fastening the annular member against the flange, with the skin segment being located between them to provide a fluid-tight seal at the end of the tubular reservoir with the skin being attached over the end of the reservoir as in a drum. Since fleshly harvested skin is resilient, no additional seal is required, but a flexible sealing member (such as an O-ring) can be provided between, e.g., the flange and annular member, if desired.

The two embodiments described above are exemplified in FIGS. 1 and 2, in which the same reference numerals refer to corresponding features of the different embodiments.

FIG. 1 shows a first embodiment of an apparatus of the invention in which nutrient reservoir 10 is supported by legs 20. Skin segment 30 is held in place by clamps 40 attached via wires 60 than run over pulleys 50 to freely suspended weights 70. Nutrient medium 80 is present in reservoir 10 in an amount sufficient to cover skin segment 30.

Figure 2:
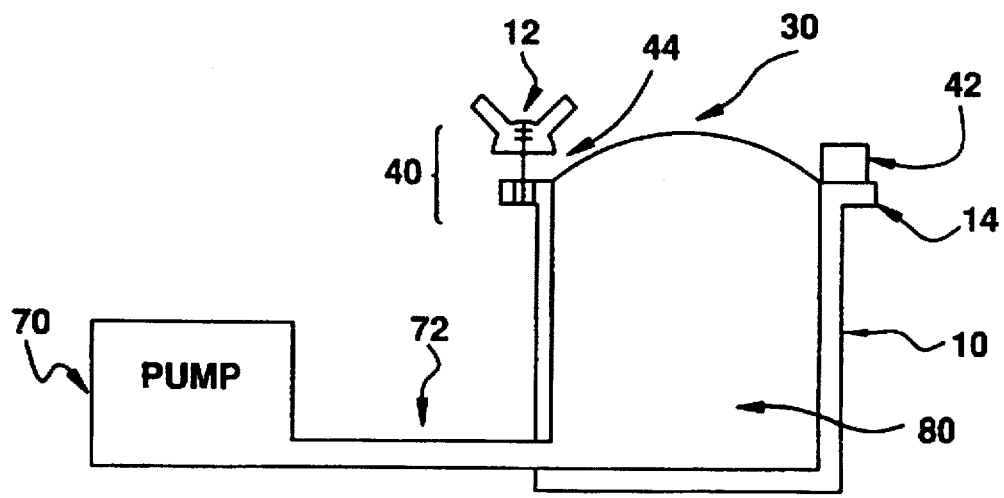
FIG. 2 is a vertical cross-sectional view of a second embodiment of an apparatus of the invention.

FIG. 2 shows a second embodiment of an apparatus of the invention in which tubular reservoir 10 contains nutrient medium 80. Skin segment 30 is held in place over the end of reservoir 10 by clamp 40, which in this embodiment is an annular member 42 having grooves 44 that match with and engage pivoted wing bolts 12 that are attached to flange 14 at the end of reservoir 10. Hydraulic pressure is supplied by pump 70 that is fluidly connected via piping 72 to reservoir 10.

The reader is directed to any of the patents or other publications in the field of tissue culture for details of such apparatuses related to aspects of general tissue culture.

A key aspect of the invention is subjecting the detached skin segment to stretching forces while the skin segment is in the tissue culture medium. Here "stretching forces" means a force or forces applied to the skin segment in one or more direction parallel to the plane of the skin surface. Because of the physical nature of stretching forces, at least two opposed forces are applied to a skin segment (because of Newton's familiar law of equal and opposite forces). If only two opposed forces are present the stretching is along a line coaxial with the stretching forces, subject to some additional stretching along adjacent regions of the detached skin segment. This is the simplest stretching situation, but is not particularly desired because of the resulting skin deformation. Additional forces can applied to provide for more regular stretching of the skin. Parallel opposed forces (such as would be applied by two broad, rigid clamps attached to opposite ends of a detached skin segment) lead to stretching along a single dimension of the skin. Non-parallel multiple stretching forces (e.g., radial outward from a central point or orthogonally in the plane of the skin) result in stretching in both of the two dimensions of a detached skin segment (i.e., the two dimensions parallel to the plane of the skin surface).

Forces can be applied to the skin that are not entirely parallel to the skin surface; however, some portion of the force must be parallel to the skin surface for stretching to take place. For example, a convex solid surface or a fluid forced against the face of a detached skin segment whose edges are fixed will cause the skin segment to be subjected to forces both orthogonal and parallel to the surface of the skin; such stretching comes within the scope of the present invention.

While the detached skin segment is being stretched, the ends of the segment are held in place in the tissue culture by some physical apparatus. Any apparatus that can be used to hold the ends in place can be used. An attachment apparatus is need for each point to which a force will be applied. Typical attachment apparatuses include clamps, hooks, sutures, and glue. A clamp can be narrow (e.g., less than 1/10 the length of the edge being held) or broad (up to or greater than the width of the edge, and generally considered broad when greater in width than ½ the width of the edge). If opposed broad clamps are used, stretching between the ends of the clamp will generally be restricted if an orthogonal stretching force is also present on the skin. For maximum stretching efficiency, multiple attachment points capable of moving away from each other during the stretching process are preferred. For example, multiple small hooks or clamps attached in a generally circular manner to a circular detached skin segment and subjected to forces applied radially outward from the center of the segment automatically move away from each other as stretching proceeds, thus supplying stretching forces along the tangents of the circle as well as along its radii.

The forces themselves can be supplied by any means for supplying force, such as a weight, spring, or motor. The forces can be either static or dynamic. Here a static force is one which is applied between two attachment points that do not move further apart from each other as cell growth and division occurs to reduce over time the force between the attachment points. For example, two clamps can be attached to opposite ends of a detached skin segment, with one (or both) of the clamps being attached to a screw that the distance between the clamps can be varied. Turning the screw to move the clamped ends away from each other produces an initial force on the skin segment, but this force decreases as cells in the skin grow and divide. A dynamic force, on the other hand, is one provided between two attachment points that are capable of movement so that a constant force can be maintained. For example, two clamps can be attached to weights that are suspended via a pulley system from opposite ends of a detached skin segment. The force on the skin segment in such an apparatus remains constant as the skin grows and divides.

The amount of the force applied to the skin is minimally that required to cause the skin to stretch and will not exceed the amount required to cause the skin to rupture. Since the strength of different skin segments obtained from the same donor vary, the forces are best determined empirically by the amount of skin stretch that is obtained. In many cases, the actual forces will never even be measured or known, such as in a screw-based apparatus. A typical stretched skin segment has an area after being subjected to stretching forces (over an appropriate length of time) that is at least twice that of the skin segment prior to being subjected to the stretching forces. For human skin, stretching of at least 2% per day is desired, preferably at least 5%, more preferably at least 10%. Non-human skin can be either tougher or less tough (here "tough" refers to resistance to stretching) than human skin and thus may be stretched correspondingly less or more than these amounts. In general skin can be stretched until rupture or cell death induced by the tension of stretching, which can readily be followed by histological examination. In some cases it may be desirable to keep stretching under 15% per day to avoid cell death, in other cases under 12%. However, the maximum sustainable stretch rate is best determined empirically, using these numbers as initial guidelines. When skin is initially placed in the nutrient medium, it should be stretched back to in original in vivo size before actual stretching is measured, since skin removed from a body generally shrinks to about one-half of its original dimensions. When hair- or fur-bearing skin is being grown, an additional factor to be considered is selecting a stretch rate is the rate of generation of new hair follicles, which will occur along with other cell growth and division in full-thickness skin. The rate of stretching can be selected in such cases to provide the desired fur (hair) density, rather than simply selecting for the maximum sustainable stretch rate.

After the stretched skin segment has regrown its original thickness, the skin segment can be used as a graft or be divided into further segments so that one or more of the further segments is subjected again to the method of the invention. As long as cell growth continues, new normal skin can be produced from parts of the original donor graft. Skin having a surface are at least two times that of the original donated skin segment can be provided in one stretching operation (which may last over several days), usually at least four times, and often at least eight that of the original. Since the stretched skin can then be divided and and the resulting segments re-stretched, exponential production of skin is possible.

Once a stretched skin graft product has been prepared, it is used in skin grafting in the same manner as an unstretched graft donor skin segment. Fur-bearing skin can be used in the normal manner of using animal pelts for making fur garments.

The invention now being generally described, the same will be better understood by reference to the following detailed examples of the invention, which are provided here for illustration only and are not to be considered limiting of the invention unless so specified.

EXAMPLE

MATERIALS AND METHODS

Sprague-Dawley rats are used for harvesting and placement of the treated skin grafts. All surgical procedures are carried out under general anesthesia following standard laboratory techniques and animal care guidelines. Each rat is anesthetized with pentobarbital 50 mg/kg intraperitoneally. A full thickness ventral skin graft is then harvested using standard aseptic technique, and the wound is closed with absorbable suture. One half of these grafts are thinned to split thickness grafts using the Reese dermatome, and one half of the grafts are treated as full thickness grafts. The animals are observed until awake and ambulating and are then returned to their housing facility.

Skin grafts are measured in size before and after harvesting and are then stretched in vitro using different types of skin stretching devices. Stretching generally utilizes a daily increase in the expansion distance. All grafts are placed in Dulbecco's modified Eagle's medium (DMEM) optionally containing 10% fetal bovine serum and placed on sterile petri dishes during expansion. In some experiments 10% fetal calf serum is added to the mixture, as it provides many nutrients desirable for maximum rate of cell growth. To maintain a constant environment for skin graft support during stretching, the grafts are stored in an incubator at 37° C. with an atmosphere containing 5% carbon dioxide. The grafts are observed and stretched daily, and the growth medium is replaced every other day.

The skin graft expansion are divided into groups. One group of full and split thickness grafts is stretched initially to 2× normal size. A second group is stretched to 4× normal, and a third group to 8× normal size. Some grafts are stretched further.

Initial studies are carried out at 37° C. (human core temperature). However, lower temperatures can be used to slow metabolism of the skin graft and increase the viability, "stretchability," and growth potential.

After stretching of the skin grafts and recovery of the skin to its original state, the animals are again anesthetized with pentobarbital. The skin grafts are attached to the dorsal surface of the animal after a surgical defect in the skin is created by simple skin excision. The size of the graft is measured and recorded at the time of grafting. The animals are monitored daily until postoperative day 14 to examine skin graft take and contracture of the graft. At postoperative day 14 the animals are sacrificed and paper patterns are made of the surviving skin graft area and its size. The size of the surviving area is compared to that removed at the initial procedure and that grafted after in-vitro stretching. A group of non-expanded grafts that are placed in DMEM are used as controls. The experimental animals are compared with the controls using standard statistical methods to look for any deviation of the means. The number of animals used is selected to produce a statistically significant result without excess animal sacrifice. In typical studies done previously, between 10 and 30 animals have been used for statistical significance to be evident. The standard deviation in the control group will vary moderately because of differential survival of skin grafts even by standard techniques. A sample size of 20 experimental rats will generally provide a sample large enough to ensure statistical analysis.

RESULTS

Results obtained to date verify the premise of the invention. Ventral rat full-thickness skin grafts were harvested and split with a Reese dermatome to provide split-thickness skin segments. Full-thickness skin graft segments were used as well. The rat skin grafts of approximately 4 cm square (prior to harvest) were stretched in vitro by wrapping the graft around a tissue expander (essentially an expandable balloon), and the graft sutured to itself around the expander using absorbable suture. The expander with the graft around it was placed in a bath of tissue culture medium (DMEM) and placed in an incubator at 37° C. Every day the expander was removed from the bath, and water was injected into the expander to cause further expansion. The experiment was stopped when the sutures tore through the graft. However, the expanded skin showed marked increase in size with daily inflation of the expanders, so that by the end of one week, almost a 2-fold increase in surface area was noted. This success rate was repeated several times.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of growing complete vertebrate skin in vitro, which comprises:

obtaining a detached segment of vertebrate skin comprising an epidermal layer and a dermal layer and having a first surface area;

positioning said skin segment in an artificial cell-growth medium containing sufficient nutrients to maintain growth of cells of said skin;

subjecting said skin segment to stretching forces while said skin segment is in said medium; and collecting said skin after said skin has grown to have an expanded surface area greater than said first surface area and to have dermal and epidermal layers over said expanded surface area.

2. The method of claim 1, wherein said stretching forces stretch said skin segment in one dimension.

3. The method of claim 1, wherein said stretching forces stretch said skin segment in two dimension.

4. The method of claim 1, wherein said skin segment has an area after being subjected to said stretching forces at least twice that of said skin segment prior to being subjected to said stretching forces.

5. The method of claim 1, wherein said skin segment is subjected to static stretching forces.

6. The method of claim 5, wherein after said skin segment has regrown full thickness, said skin segment is divided into further segments, and at least one of said further segments is subjected to said method.

7. The method of claim 1, wherein said skin segment is subjected to dynamic stretching forces.

8. The method of claim 1, wherein said skin segment is mammalian skin.

9. The method of claim 8, wherein said skin segment is human skin.

10. A detached skin segment having a dermal layer and an epidermal layer and being produced by the method of claim 1.

* * * * *